(12) United States Patent
Arthur et al.

(10) Patent No.: US 7,419,060 B2
(45) Date of Patent: Sep. 2, 2008

(54) INTEGRATED FUEL CONTAINER AND IMPURITY REMOVAL CARTRIDGE

(75) Inventors: Alan R Arthur, Salem, OR (US); Philip H. Harding, Albany, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 511 days.

(21) Appl. No.: 10/382,701

(22) Filed: Mar. 5, 2003

(65) Prior Publication Data

US 2004/0175600 A1 Sep. 9, 2004

(51) Int. Cl.
*B01D 35/00* (2006.01)
*H01M 8/00* (2006.01)

(52) U.S. Cl. .............. 210/429; 210/430; 210/435; 210/441; 210/502.1; 210/510.1; 429/12

(58) Field of Classification Search ............. 210/429, 210/430, 435, 441, 442, 446, 473, 502.1, 210/510.1, 500.26, 500.27, DIG. 17; 422/211; 204/155; 429/12, 13, 17
See application file for complete search history.

(56) References Cited

U.S. PATENT DOCUMENTS

| | | | | |
|---|---|---|---|---|
| 3,004,670 A | * | 10/1961 | Zonker | 210/429 |
| 3,250,242 A | * | 5/1966 | Pekarek | 116/267 |
| 4,112,984 A | * | 9/1978 | Guglia et al. | 141/98 |
| 4,522,159 A | * | 6/1985 | Engel et al. | 123/1 A |
| 5,354,362 A | * | 10/1994 | Sowinski | 95/127 |
| 5,879,826 A | | 3/1999 | Lehman et al. | |
| 5,928,512 A | * | 7/1999 | Hatch et al. | 210/266 |
| 5,938,800 A | * | 8/1999 | Verrill et al. | 48/127.9 |
| 6,098,652 A | * | 8/2000 | Brandt | 137/315.05 |
| 6,183,895 B1 | * | 2/2001 | Kudo et al. | 429/20 |
| 6,221,117 B1 | | 4/2001 | Edlund et al. | |
| 6,247,486 B1 | * | 6/2001 | Schwegler et al. | 137/115.27 |
| 6,492,050 B1 | | 12/2002 | Sammes | |
| 6,780,534 B2 | * | 8/2004 | Stenersen et al. | 429/19 |
| 6,861,002 B2 | * | 3/2005 | Hughes | 210/681 |
| 2002/0090538 A1 | * | 7/2002 | Schaefer et al. | 429/13 |
| 2003/0113598 A1 | * | 6/2003 | Chow et al. | 429/17 |
| 2004/0094488 A1 | * | 5/2004 | Grant | 210/791 |

FOREIGN PATENT DOCUMENTS

| | | |
|---|---|---|
| DE | 199 219 816 | 10/2000 |
| DE | 100 40 011 | 2/2001 |
| JP | 8-247439 | * 9/1996 |
| JP | 2002-83623 A | * 3/2002 |

OTHER PUBLICATIONS

English abstract of JP 8-247439.*
English abstract of JP 2002-83623 A.*

* cited by examiner

*Primary Examiner*—John Kim

(57) ABSTRACT

A fuel supply for a fuel cell including a fuel container and an impurity removal cartridge connected to the fuel container, where both the fuel container and the impurity removal cartridge are integrated into a single unit.

36 Claims, 7 Drawing Sheets

INTEGRATED FUEL CONTAINER AND IMPURITY REMOVAL CARTRIDGE

BACKGROUND

During the past several years, the popularity and viability of fuel cells for producing large and small amounts of electricity has increased significantly. Fuel cells conduct an electrochemical reaction with chemicals such as hydrogen and oxygen to produce electricity and heat. Fuel cells are similar to batteries, but fuel cells can be "recharged" while providing power and are much cooler and cleaner than devices that combust hydrocarbons. Fuel cells provide a DC (direct current) voltage that may be used to power motors, lights, computers, or any number of electrical appliances. There are several different types of fuel cells, each using a different chemistry. Fuel cells are usually classified by the type of electrolyte used. The fuel cell types are generally categorized into one of five groups: proton exchange membrane (PEM) fuel cells, alkaline fuel cells (AFC), phosphoric-acid fuel cells (PAFC), solid oxide fuel cells (SOFC), and molten carbonate fuel cells (MCFC).

Each of the fuel cells mentioned above uses oxygen and hydrogen to produce electricity. Ambient air typically supplies the oxygen for a fuel cell. In fact, for the PEM fuel cell, ordinary air may be pumped directly into the cathode of the fuel cell. However, hydrogen is not as readily available as oxygen. Hydrogen is difficult to generate, store, and distribute for a number of reasons and is generally handled with appropriate precautions to reduce potential safety hazards.

One common method for producing hydrogen for fuel cells is through the use of a reformer. A reformer is fed hydrocarbons or other fuels from which hydrogen is produced. The hydrogen produced by the reformer can then be fed to a fuel cell and processed with oxygen to produce the desired electricity. The use of a reformer allows for the production of hydrogen from propane, butane, or a number of other readily accessible natural gases that serve as the hydrogen fuel source.

Since many common hydrocarbon gases are not readily detectible by human senses, odorizing agents such as sulfur are typically included with the hydrocarbons as a safety feature. If a leak of the hydrocarbons occurs, the leak may be readily detected by smelling the odorizing agent. In some instances, sulfur can occur as a natural constituent of the gaseous fuels. However, many consumer grade hydrocarbons produce undesirable byproducts such as $SO_x$ and $NO_x$. These by-products are not only pollutants but may also damage the reformer of a fuel cell system. Sulfur, in particular, must be removed from the fuel being fed to the reformer or damage may occur to the electrode catalyst.

One possible solution to prevent sulfur from reaching the reformer and subsequently the electrode catalyst is to use deodorized fuels as the hydrogen source. However, by deodorizing the fuels used to generate hydrogen, it becomes impossible to smell a fuel leak. If a leak goes undetected because it is imperceptible, the hazards and potential damage that may be caused by the leak are greatly increased. This would likely result in additional shipping, storage, and usage restrictions on the fuel, thereby increasing the fuel cost.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

An apparatus for integrating a fuel cell fuel supply and a fuel supply cleaner is described herein. According to one exemplary implementation, described more fully below, a fuel supply and an impurity removal cartridge are integrated such that they may both be removed from a fuel cell system as a single functional unit while continuing to provide odor-enhanced leak detection.

In the following description, for purposes of explanation, numerous specific details are set forth in order to provide a thorough understanding of the invention. It will be apparent, however, to one skilled in the art that the invention may be practiced without these specific details. Reference in the specification to "one embodiment" or "an embodiment" means that a particular feature, structure, or characteristic described in connection with the embodiment is included in at least one embodiment of the invention. The appearance of the phrase "in one embodiment" in various places in the specification are not necessarily all referring to the same embodiment.

Figure 1:
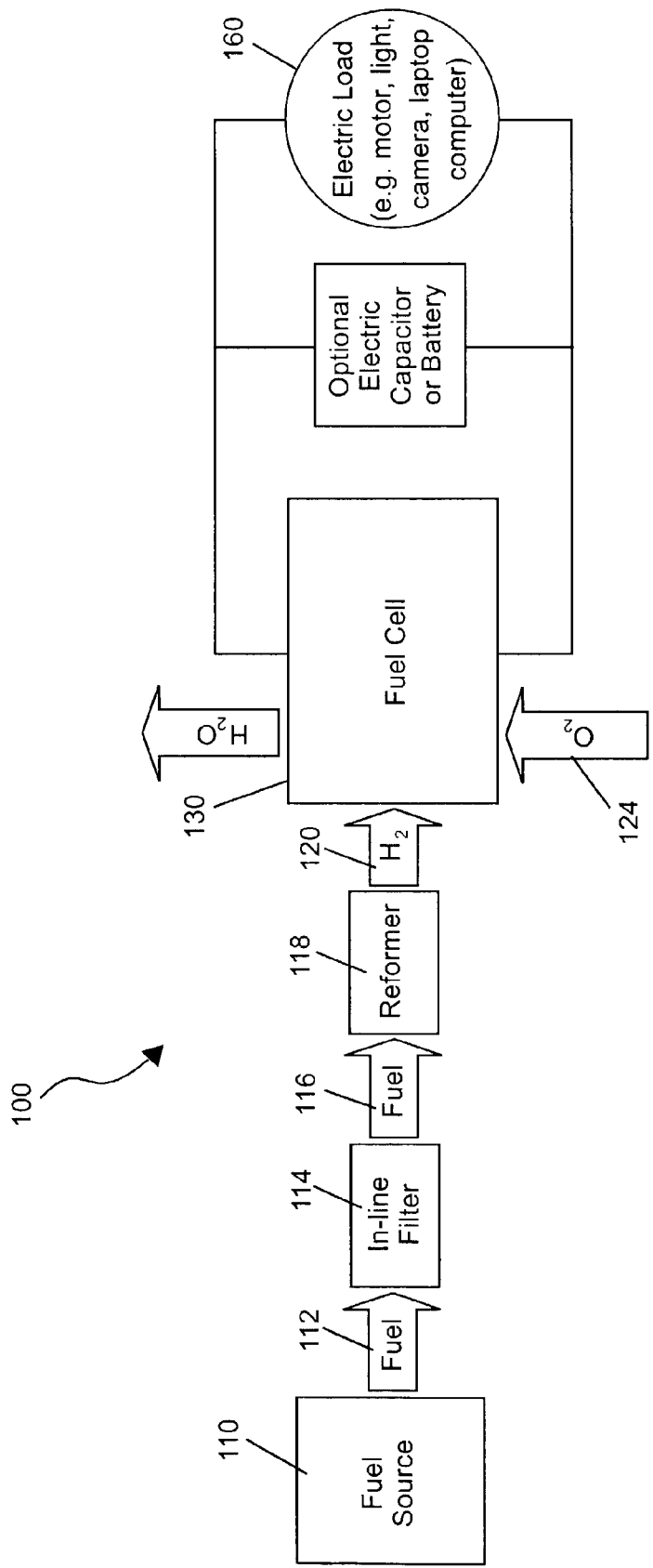
FIG. 1 illustrates a prior art system for removing sulfur from hydrocarbon fuels.

An alternative solution to eliminating the sulfur that reaches the reformer is illustrated in FIG. 1. As shown in FIG. 1, a fuel cell (100) receives fuel from a fuel source (110). Typically, the fuel source (110) supplies consumer grade hydrocarbons such as propane or butane as fuel (112). The consumer grade hydrocarbons typically include an odorizing agent for the safety reasons mentioned above. Prior to entering the reformer (118), the consumer grade fuel (112) passes through an in-line filter (114) or other form of sulfur scrubber physically located just prior to the reformer (118).

Once the sulfur passes through the filter (114), it exits as deodorized fuel (116). The deodorized fuel (116) may then be fed into and processed by the reformer (118) to produce hydrogen (120). The resulting hydrogen (120) may then be mixed with oxygen (124) in the fuel cell (130) to generate and supply electricity to an electrical load (160) such as a motor or a light. In some embodiments, a capacitor or battery may be connected in parallel with the fuel cell and electrical load to provide power to the load (160) when the fuel cell (130) is starting up or inoperative.

By deodorizing the fuel (116) prior to its introduction to the reformer (118), the likelihood of damage caused by sulfur and other unwanted pollutants is greatly reduced. However, the in-line filter (114) that is placed in line with the flow of the hydrocarbon fuel (112) typically requires frequent maintenance and/or removal. This continual need for maintenance of the sulfur scrubbing in-line filter (114) is an inconvenience to users.

Exemplary Structure

Figure 2:
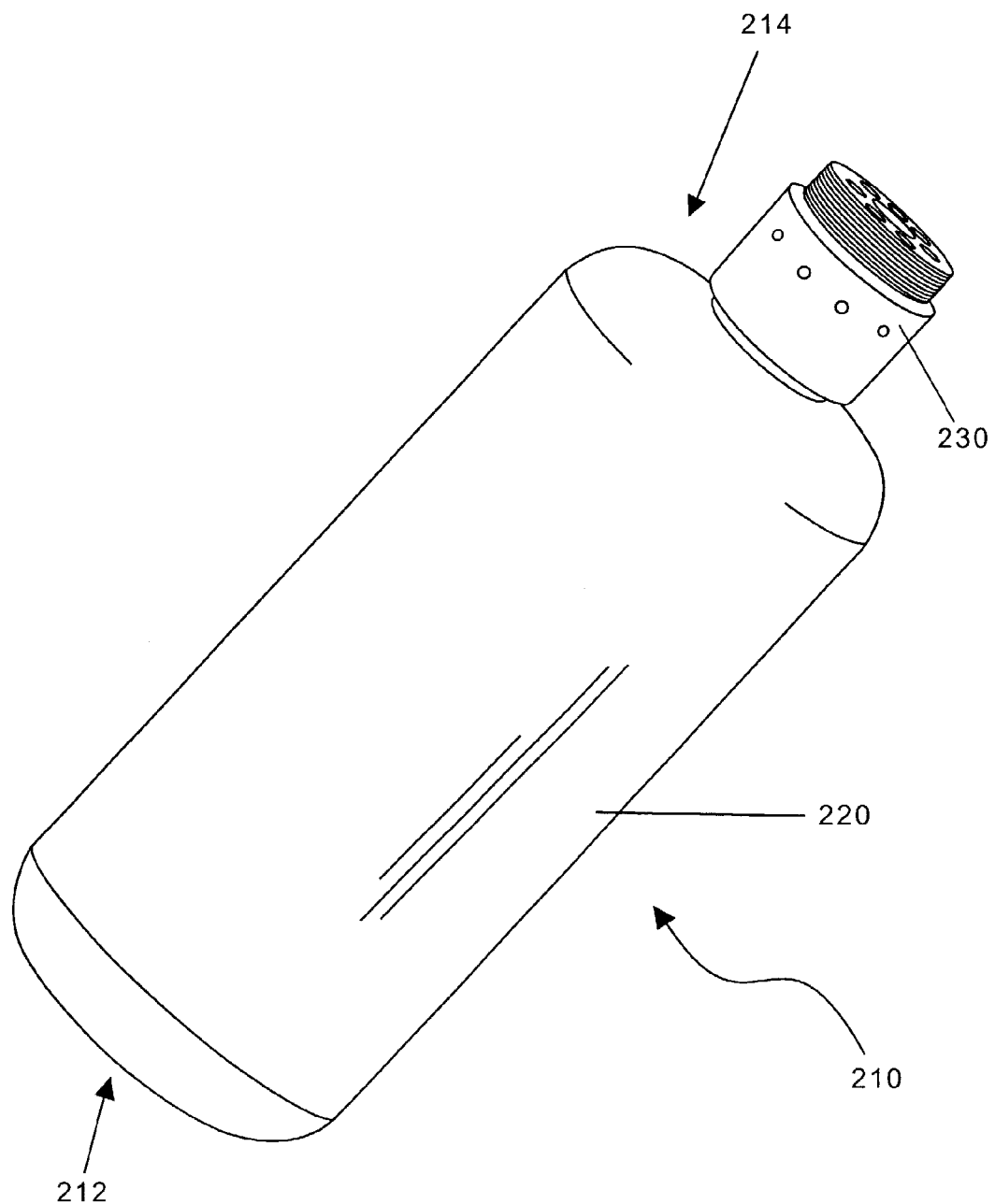
FIG. 2 illustrates an integrated fuel container and sulfur removal cartridge according to one embodiment of the present invention.

FIG. 2 illustrates an embodiment of a fuel source capable of providing fuel to, for example, a fuel cell. As shown in FIG. 2, one embodiment of the fuel source may include both a fuel container (210) and an impurity removal cartridge (230), e.g., an odorant removal cartridge (230) for an odorant such as sulfur. The fuel container (210) may either be integrally formed with the cartridge (230), or both the fuel container (210) and the cartridge (230) may be formed separately and later coupled.

The fuel container (210) of the embodiment illustrated in FIG. 2 may be a cylindrically shaped fuel container (210) that contains pressurized hydrocarbons, such as propane or butane, and an odorizing agent, such as sulfur. The fuel container (210) may be formed with a body (220) having a distal end (212) and a proximal end (214). If the container (210) and the impurity removal cartridge (230) are formed as separate units, the proximal end (214) of the fuel container (210) includes a means for fluidly coupling the fuel container (210) to the impurity removal cartridge (230), a fuel cell, or any other device that may be fluidly coupled to a fuel source.

FIG. 2 shows the impurity removal cartridge (230) fluidly coupled to the proximal end (214) of the fuel container (210) according to one embodiment of the fuel source. The fuel container (210) may be fluidly coupled to the impurity removal cartridge (230) using any number of coupling means including, but in no way limited to threads, adhesive, clamps or other mechanical devices.

Figure 3:
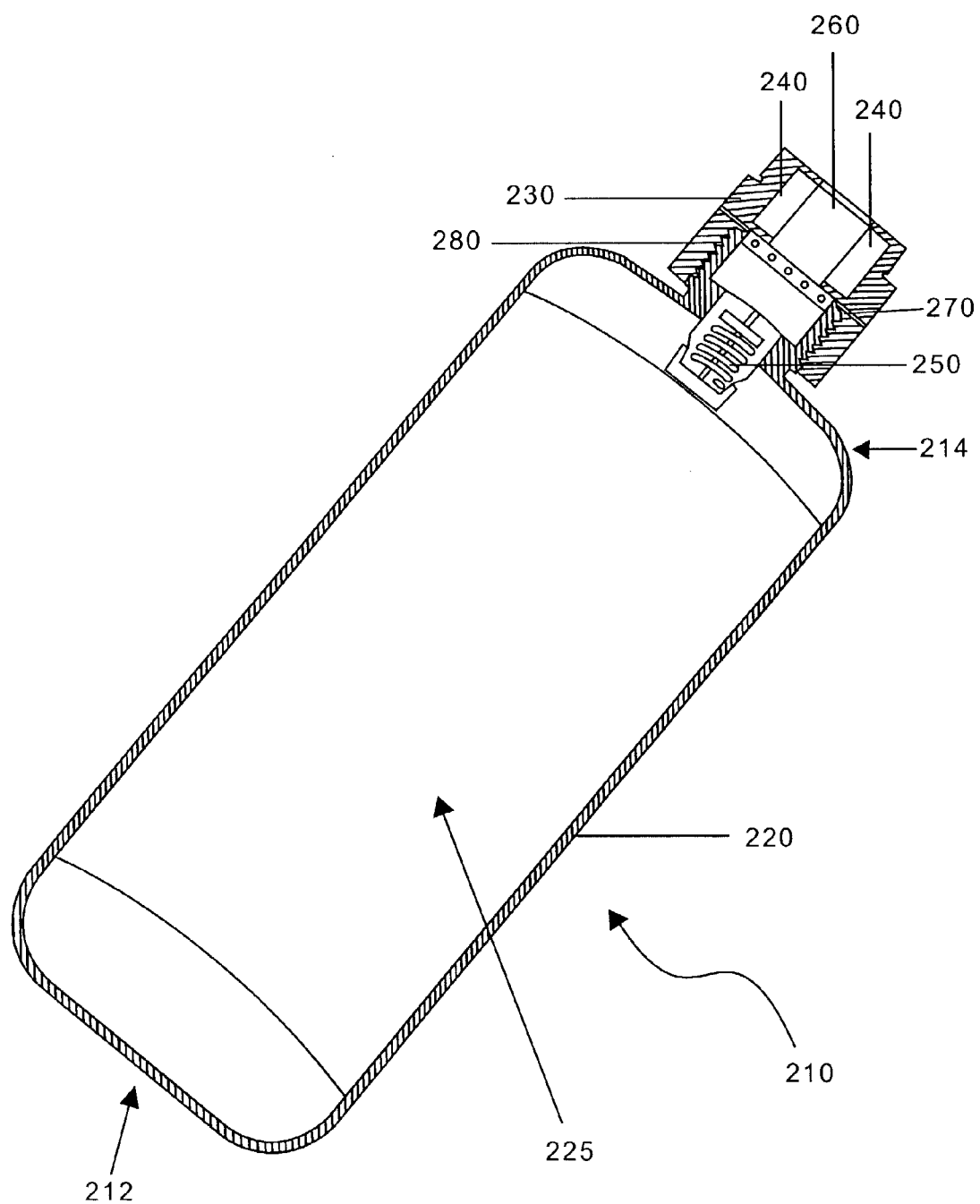
FIG. 3 illustrates internal components of an integrated fuel container system and sulfur removal cartridge according to one embodiment of the present invention.

FIG. 3 further illustrates the components of the integrated fuel supply and fuel supply cleaner. As shown in FIG. 3, the fuel container (210) includes an internal cavity (225) for storing pressurized fuel until it is released into a fuel-using system. The proximal end (214) of the fuel container (210) further includes a coupling device (280) and a valve (250). The valve (250) forms a portion of the coupling device (280) of the fuel container (210). The valve (250) of the fuel container (210) is used to regulate the release of pressurized fuel from the fuel container (210) into a fuel-using system.

The valve (250) illustrated in FIG. 3 is a Schrader style valve, however, any valve for regulating the emission of pressurized fuels may be used in the present fuel supply. The coupling device (280) illustrated in FIG. 3 is an externally threaded segment located on the proximal end (214) of the fuel container (210). The coupling device (280) may couple the fuel container (210) to the impurity removal cartridge (230) and subsequently to the rest of the system. While the present fuel supply (210) is shown using threads as the means for coupling the fuel container (210) and the impurity removal cartridge (230) to the system, other coupling means may be used.

FIG. 3 also illustrates the internal components of one embodiment of the impurity removal cartridge (230). As shown in FIG. 3, the impurity removal cartridge (230) includes an actuator orifice (260) located along the center axis of the body of the impurity removal cartridge (230). The impurity removal cartridge (230) also includes a sulfur removing adsorbent (240) that is substantially contained within the body of the impurity removal cartridge (230).

A number of radially routed orifices (270) are also located on the body of the impurity removal cartridge (230) just below the sulfur removing absorbent (240). The radially routed orifices (270) extend radially from the center of the body of the impurity removal cartridge (230) to the outer surface of the impurity removal cartridge (230) providing a fluid communication channel to the outer surface of the impurity removal cartridge (230).

Figure 4:
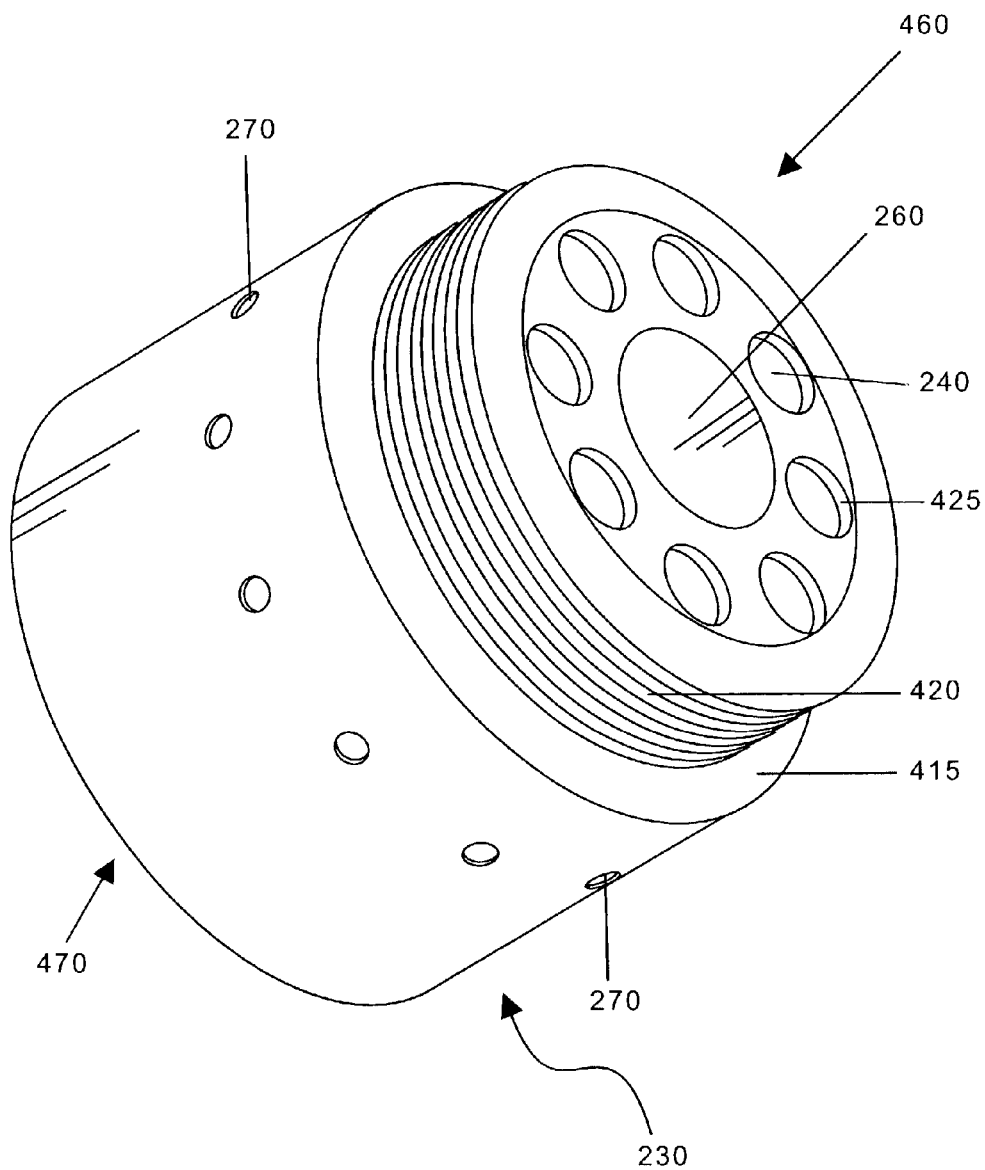
FIG. 4 illustrates a sulfur removal cartridge according to one embodiment of the present invention.

FIG. 4 is a view of an impurity removal cartridge (230) according to one embodiment of the integrated fuel supply and fuel supply cleaner. As shown in FIG. 4, the impurity removal cartridge (230) includes a cylindrically shaped body with both a distal end (470) and a proximal end (460).

The proximal end (460) is a substantially flat surface with an actuator orifice (260) formed at the center. The actuator orifice (260) extends the entire length of the impurity removal cartridge body (230) along the center axis. The actuator orifice (260) receives an actuator when the impurity removal cartridge and fuel container are coupled to a fuel-using system and provides a leak detection channel when in storage.

A number of external axially routed orifices (425) are also located on the face of the proximal end (460), which extend axially into the body of the impurity removal cartridge (230). These external axially routed orifices (425) may have a circular cross section and extend only a short distance into the body of the impurity removal cartridge (230). The external axial routing orifices (425) provide for the flow of any fuel that has passed through the body of the impurity removal cartridge (230).

FIG. 4 also illustrates external threads (420) located on the outer surface of the proximal end (460) of the impurity removal cartridge body (230). The external threads (420) are included as part of the impurity removal cartridge (230) to allow the impurity removal cartridge (230) to be fluidly coupled to a fuel cell or other fuel-using system. Any coupling means may be used that are capable of providing fluid communication to couple the impurity removal cartridge (230) to a fuel-using system.

On the distal end (470) of the impurity removal cartridge (230), immediately adjacent to the external threads (420), is a lip (415). The lip (415) provides a stopping surface for any coupling device that is fluidly coupled to the impurity removal cartridge (230) using the external threads (420). Between the distal end (470) of the cartridge (230) and the lip (415), there are a number of radially routed orifices (270) that extend from the center of the impurity removal cartridge (230) to the outer surface of the cartridge (230) and provide a fluid communication channel. While the present embodiment of the impurity removal cartridge (230) has been explained as having a cylindrical body shape, it is possible for the impurity removal cartridge (230) to be any shape capable of being received by the coupler of a fuel-using system. Moreover, the impurity removal cartridge (230) may be constructed of plastic, metal, ceramic, composite, any combination thereof or similar materials.

Figure 5:
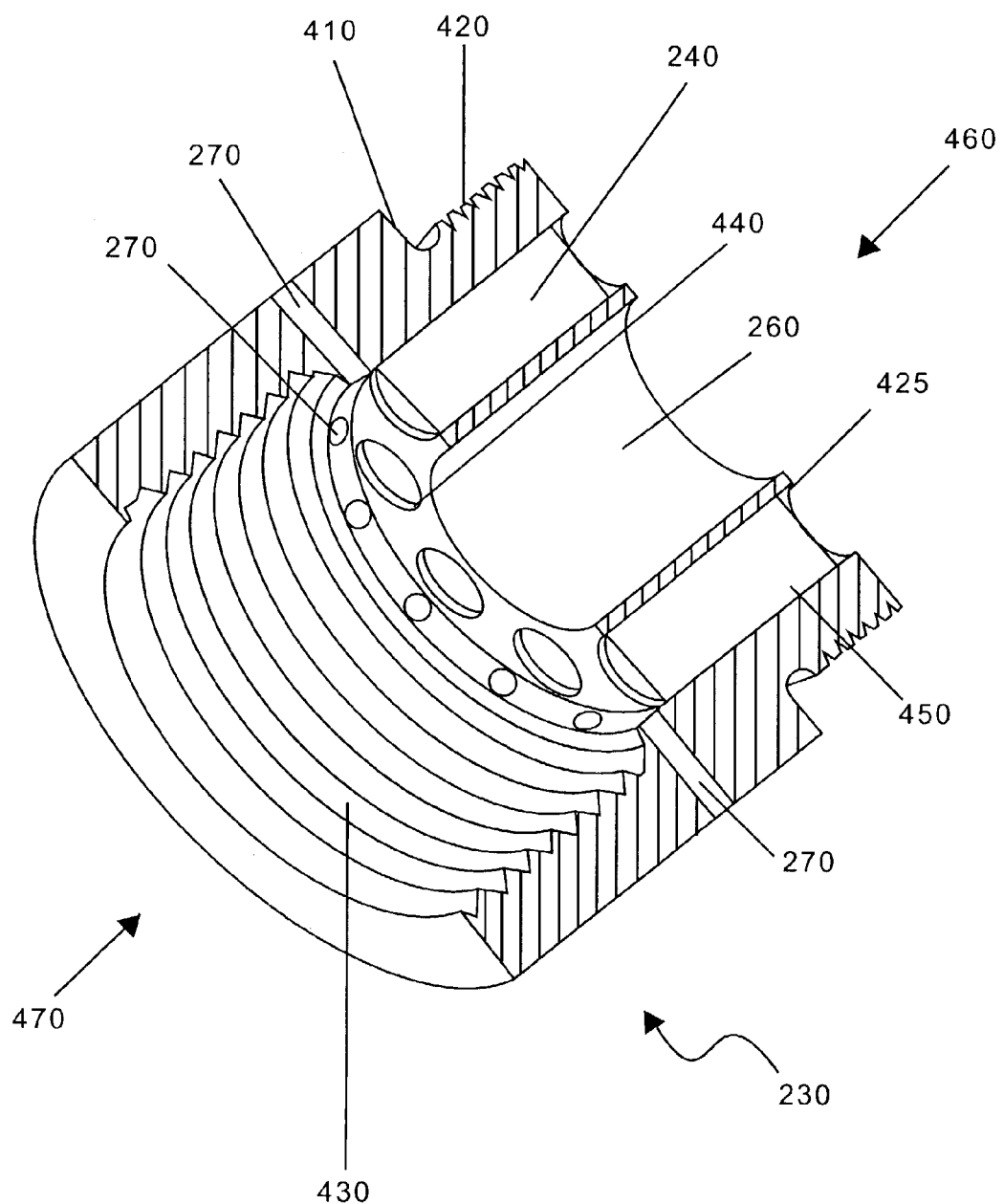
FIG. 5 is a cross-sectional view of a sulfur removal cartridge according to one embodiment of the present invention.

FIG. 5 is a cross sectional view of one embodiment of an impurity removal cartridge (230) illustrating the structural components of the impurity removal cartridge (230). As shown in FIG. 5, the distal end (470) of the impurity removal cartridge (230) includes a receiver cavity (430) for receiving the coupling means of a fuel container (280; FIG. 3) or other fuel supply. Included in the receiver cavity (430) is a means for receiving and fluidly coupling the impurity removal cartridge (230) to the fuel container (210; FIG. 3).

The coupling means shown in FIG. 5 is a series of threads formed on the inner wall of the receiver cavity (430). However, the coupling means of the receiver cavity (430) may be any coupling means capable of fluidly coupling the impurity removal cartridge (230) to a fuel container (210; FIG. 3). On the proximal end of the receiver cavity (430) is one or more radially routed orifices (270) that radially extend from the inner wall of the impurity removal cartridge (230) to the outer wall of the impurity removal cartridge (230). The radially routed orifices (270) provide a fluid communication channel for any pressurized fuels that enter the receiver cavity (430) to the outer wall of the impurity removal cartridge (230). The function of the radially routed orifices (270) is further explained below.

Perpendicular to the radially routed orifices (270) are a number of internal axially routing orifices (440) that are also in fluid communication with any pressurized fuels that enter the receiver cavity (430). The internal axially routing orifices (440) are fluidly coupled to a filter-containing cavity (450) as shown in FIG. 5. The filter-containing cavity (450) shown in FIG. 5 is fluidly coupled to both the inner (440) and outer (425) axial routing orifices providing a fuel flow path from the receiver cavity (430) to a fuel-using system. A fuel-filtering material (240), such as a sulfur removing adsorbent, is substantially contained within the filter-containing cavity (450).

The fuel-filtering material (240) contained within the filter-containing cavity (450) removes sulfur or any other odorizing agent from pressurized fuel. The fuel-filtering material (240) may be a porous matrix material. Specifically, the fuel-filtering material (240) may be, but is in no way limited to, a zeolite-based filter, calcium-based adsorbents, zinc oxide, activated carbon, or any other wet or dry filter capable of removing odorizing agents from fuel. The sulfur removing adsorbent of the present integrated fuel supply and fuel supply cleaner may be a zeolite-based filter. Zeolites are highly crystalline alumino-silicate frameworks that form a highly crystalline, microporous adsorbent. The zeolites have an internal structure that may be easily tailored to adsorb any number of odorizing agents. The pore size distribution of the zeolites may be modified, enabling the zeolite to be used as a so-called molecular sieve. Molecules that are too large to diffuse into the pores, such as odorizing agents, are excluded while molecules that have a kinetic diameter smaller than the pore size diffuse into the pores and are able to pass through without the larger odorizing agents.

Figure 6:
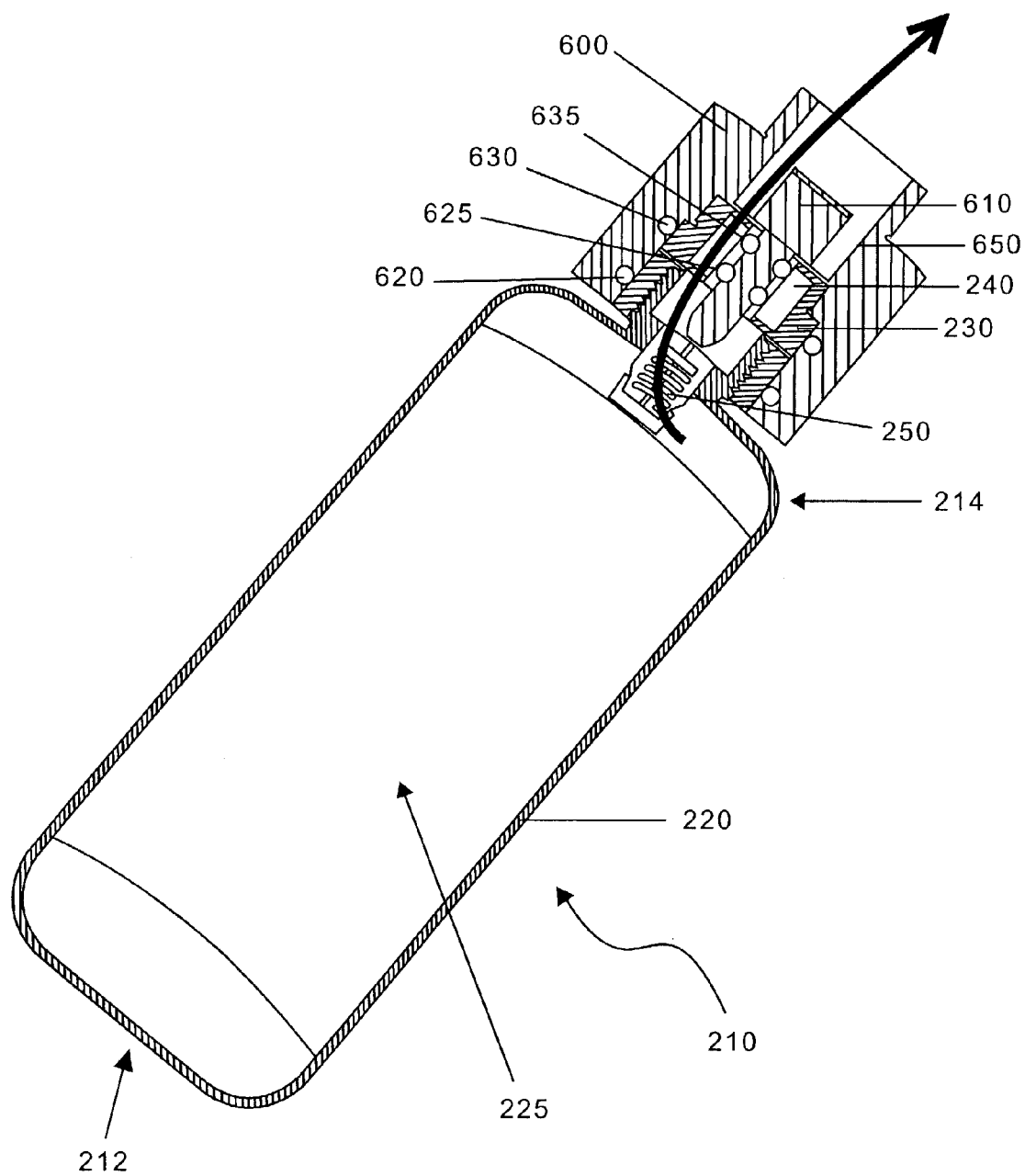
FIG. 6 illustrates the proper flow of a hydrocarbon gas according to one embodiment of the present invention.

FIG. 6 illustrates how the fuel container (210) and the impurity removal cartridge (230) are fluidly coupled to each other and to a fuel-using system. Beginning with the fuel container (210), the proximal end (214) of the fuel container (210) is fluidly coupled to the distal end of the impurity removal cartridge (230). As shown in FIG. 6, the coupling device of the fuel container (210) is inserted and coupled to the receiver cavity (430; FIG. 5) of the impurity removal cartridge (230).

While the coupling means illustrated in FIG. 6 is a threaded system, any fluid coupling means is within the scope of the present system. The fluid system coupler (600) is then fluidly coupled to the proximal end of the impurity removal cartridge (230). The fluid system coupler (600) illustrated in FIG. 6 is consistent with fluid system couplers known and used in the industry. As shown in FIG. 6, the fluid system coupler (600) includes a body with a distal and a proximal end. The distal end of the fluid system coupler (600) includes a reception orifice that protrudes axially into the body of the fluid system coupler (600) and is large enough to receive the body of the impurity removal cartridge (230). The distal end of the fluid system coupler (600) may be coupled to the proximal end of the impurity removal cartridge (230) by a threaded or any other type of coupling system.

A valve actuator (610) is formed along the center axis of the fluid system coupler (600) body to engage the valve (250) of the fuel container (210). The fluid system coupler (600) also includes a number of fuel flow path orifices (650) on each side of the valve actuator (610). The fuel flow path orifices (650) receive any fuel that has passed through the fuel-filtering material (240) of the impurity removal cartridge (230) and introduce the fuel into the fuel-using system.

A number of o-rings (620, 625, 630, 635) also form a part of the fluid system coupler (600). The two inner o-rings (625, 635) are located on the valve actuator (610) as illustrated in FIG. 6. When the fluid system coupler (600) is coupled to the impurity removal cartridge (230) the inner o-rings (625, 635) form a fluid seal between the valve actuator (610) and the wall of the actuator orifice (260; FIG. 5) of the impurity removal cartridge (230). The seal formed by the inner o-rings (625, 635) prevents any unfiltered fuel from passing through the actuator orifice (260; FIG. 5) of the impurity removal cartridge (230) and onto the fuel-using system without first passing through the fuel-filtering material (240).

Two outer o-rings (620, 630) are located along the outer wall of the reception orifice of the fluid system coupler (600) as shown in FIG. 6. When the fluid system coupler (600) is properly coupled with the impurity removal cartridge (230), a first outer o-ring (630) is located above the radially routed orifices (270; FIG. 5) and a second outer o-ring (620) is located below the radially routed orifices. By securing the outer o-rings (620, 630) both above and below the radially routed orifices (270; FIG. 5) of the impurity removal cartridge (230), a fluidly sealed cavity containing pressurized fuel and odorizing agents is formed when fuel flows through the fuel flow path. This fluidly sealed cavity containing both pressurized fuel and odorizing agents allows the illustrated embodiment to provide external leak detection leveraging the current standard odorizing agents used in the industry prior to their removal by the impurity removal cartridge (230).

Exemplary Implementation and Operation

FIG. 6 illustrates the proper operation of one exemplary embodiment of an impurity removal cartridge (230) when properly connected to a fuel-using system. As shown in FIG. 6, pressurized fuel and odorizing agents are contained within the internal cavity (225) of the fuel container (210). When the impurity removal cartridge (230) is coupled to the fuel container (210), the valve (250) of the fuel container (210) is not compressed, but a fluid tight seal is formed between the impurity removal cartridge (230) and the fuel container (210). The fuel container (210) and the impurity removal cartridge may be coupled and stored together for large periods of time without leaking fuel. If a fuel leak does occur during storage or before the fuel container (210) and the impurity removal cartridge (230) are properly connected to a fuel-using system, the leaking gas will enter the atmosphere through either the radially routed orifices (270; FIG. 5) or the unobstructed actuator orifice (260; FIG. 5) of the impurity removal cartridge (230). When fuel escapes the unconnected fuel container (210) and the impurity removal cartridge (230) through the radially routed orifices or the actuator orifice, the fuel is unfiltered and can thus be easily detected by its odor.

Once the fuel container (210) is properly coupled to the impurity removal cartridge (230), the impurity removal cartridge (230) may also be coupled to the fluid system coupler (600) and subsequently to a fuel-using system. When properly coupled, the valve actuator (610) of the fluid system coupler (600) extends through the actuator orifice (260; FIG. 5) and compresses the valve (250) of the fuel container (210). Once the valve (250) of the fuel container (210) is compressed, the pressurized fuel contained in the fuel container (210) is allowed to escape. As illustrated by the fuel flow arrow in FIG. 6, the pressurized fuel passes through the valve (250) of the fuel container (210) and into the impurity removal cartridge (230).

The pressurized fuel will then fill the cavity created between the fuel container (210) and the impurity removal cartridge (230) including the radially routed orifices (270, FIG. 5). During proper operation of the system, the outer o-rings (620, 630) prevent any pressurized fuel from escaping the system without being filtered. The pressurized fuel also passes through the internal axial routing orifice (440; FIG. 5) and into the filter-containing cavity (450; FIG. 5), both of which form a part of the impurity removal cartridge (230).

Once in the filter-containing cavity (450; FIG. 5), the pressurized fuel will come in contact with and pass through the fuel-filtering material (240). As the pressurized fuel passes through the fuel-filtering material (240), any odorizing agent or other impurity that is mixed with the pressurized fuel is removed. After passing through the fuel-filtering material (240), the now deodorized fuel passes through the external axial routing orifice (425; FIG. 5) and into the fuel flow path orifice (650) of the fluid system coupler (600). From the fuel flow path orifice (650), the deodorized fuel is introduced into the fuel-using system and may be further processed without damaging the system.

Figure 7:
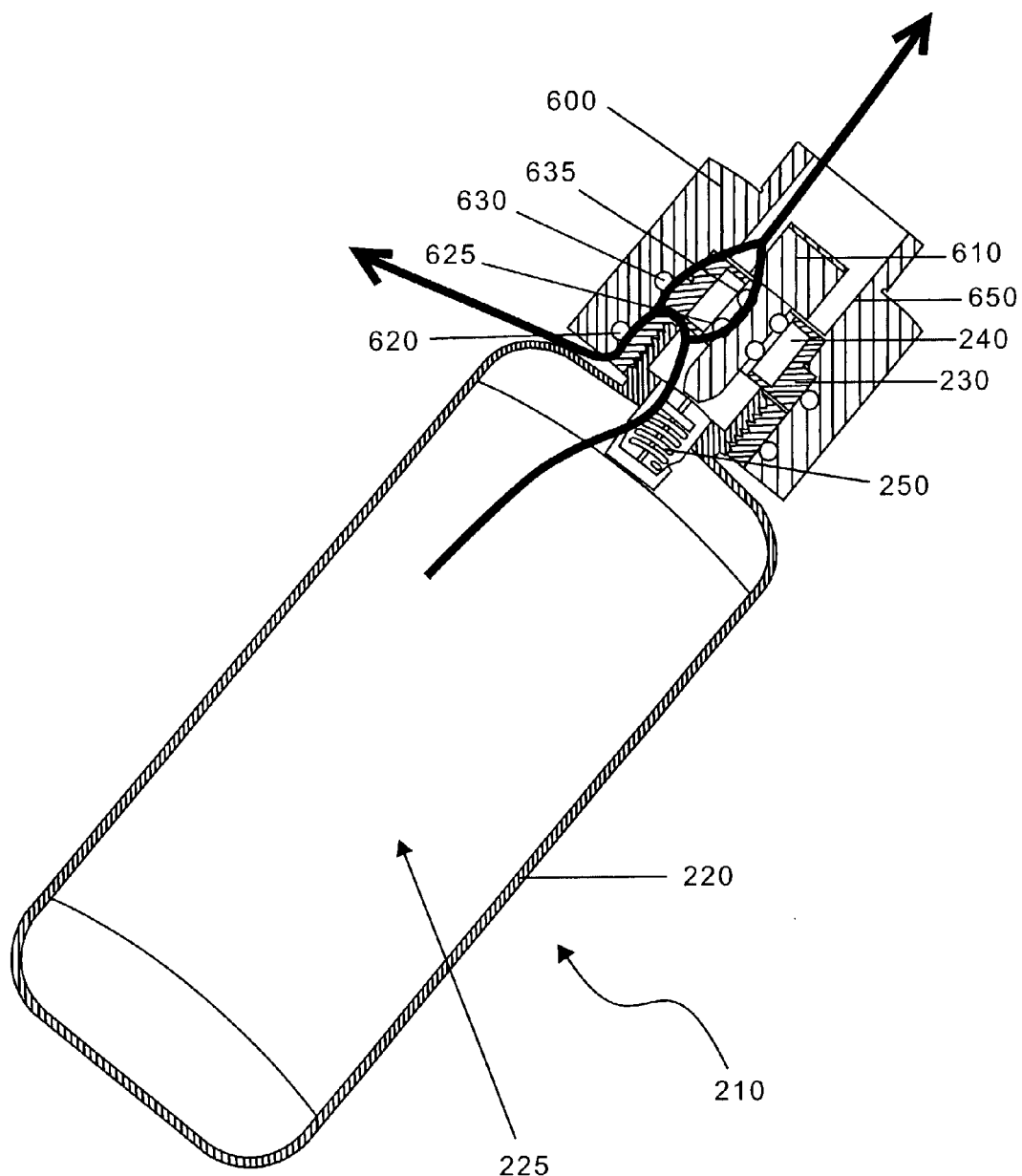
FIG. 7 illustrates possible system leak sources according to one embodiment of the present invention.

FIG. 7 illustrates possible leak sources of one embodiment of the integrated fuel supply and fuel supply cleaner system. In order to test the integrity of the fluid coupling of the fluid system coupler (600), pressurized fuel is allowed to reach the outer o-rings (620, 630) through the radial orifices (270; FIG. 5) of the impurity removal cartridge (230). If the fluid system coupler (600) does not properly seal around the impurity removal cartridge (230), pressurized fuel that has passed through the radial orifices (270; FIG. 5) may escape through the second outer o-ring (620) to the atmosphere. This leakage to the atmosphere may pose a severe fire and/or explosion hazard. The radial orifices (270; FIG. 5) are formed prior to the fuel-filtering material (240) so that any pressurized fuel that is allowed to reach the second outer o-ring (620) still contains odorizing agents. This embodiment of the impurity removal cartridge (230) allows for the detection of an external fuel leak through scent recognition of a user while still providing deodorized fuel to the system.

Once the fuel supply in the fuel container (210) has been exhausted, a user may remove both the fuel container (210) and the impurity removal cartridge (230) simultaneously as a single unit by de-coupling the fluid system coupler (600) from the impurity removal cartridge (230). Both the fuel container (210) and the impurity removal cartridge may then be replaced with both a new fuel container (210) and a new impurity removal cartridge (230). This embodiment of the integrated fuel supply allows the change out frequency of the impurity removal cartridge (230) to be the same as the life of the fuel container (210) thereby freeing the user from changing out both an in-line sulfur filter and the fuel cartridge at different times.

Alternative Embodiment

Referring again to FIG. 7, there are additional possible leakage channels that may allow odorized fuel to bypass the impurity removal cartridge (230) and enter the system fuel stream. As shown by the fuel flow arrows in FIG. 7, odorized fuel may leak past the first outer o-ring (630) or both of the inner o-rings (625, 635) and into the system fuel stream without passing through the fuel-filtering material (240). In order to prevent the further leakage of odorized fuel-into the system fuel stream, additional o-rings may be placed on various locations of the system coupler. The inclusion of additional o-rings or other sealing means will reduce the likelihood of odorized fuel leaking past the impurity removal cartridge (230).

Moreover, an in-line removable filter may also be placed within the present system as a safeguard against any odorized fuel that bypasses the impurity removal cartridge (230) due to one of the above-mentioned leaks. By placing an inline filter in the fuel path of the system, any odorizing agent that has leaked past the impurity removal cartridge (230) will be removed from the fuel prior to reaching the reformer or other system components. While the inline filter will need to be removed periodically, the incorporation of the impurity removal cartridge (230) with the fuel container (210) will greatly reduce the exposure of the inline filter to odorizing agents. As a result, the change out frequency of the inline filter will be greatly reduced. Moreover, the life of the inline filter may be designed to match the product life of the system to which it is incorporated, thereby completely eliminating the need for replacement.

In conclusion, the present invention, in its various embodiments, simultaneously reduces the maintenance needed by a fuel supply while preserving its safety features. Specifically, the present invention provides an apparatus for integrally connecting a fuel supply container to a fuel supply filter. By integrating the fuel supply container and the fuel supply filter, a user no longer needs to periodically change an in-line filter. Rather, the integrated filter may be removed and replaced each time a new fuel supply is provided. The present invention also allows non-filtered, odorized gas to be present in the system sealing means to provide an odorized source of leak detection.

The preceding description has been presented only to illustrate and describe embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A fuel cell and odorized fuel system comprising an odorant removal cartridge for use with a fuel container, said system comprising:
   a fuel cell system;
   said fuel container configured to be coupled to said fuel cell system and containing a fuel for said fuel cell system, wherein said fuel has an added odorant added to said fuel to facilitate leak detection; and
   said cartridge, wherein said cartridge comprises:
      a body with a distal and a proximal end;
      a fuel flow pat tat extends through said body from said distal end to said proximal end;
      a first coupler disposed on said distal end of said body for fluidly coupling said odorant removal cartridge to an outlet of said fuel container that is configured to hold a quantity of an odorized fuel; and
      a fuel-filtering material disposed in said fuel flow pat tat removes said odorant from fuel in said fuel flow path;
   wherein said fuel container and said odorant removal cartridge may be simultaneously replaced as a single unit.

2. The system of claim 1, wherein said first coupler comprises internal threads disposed on said distal end of said odorant removal cartridge.

3. The system af claim 1, wherein said fuel-filtering material further comprises a porous matrix material.

4. The system of claim 1, wherein said fuel-filtering material comprises a zeolite-based material.

5. The system of claim 1, wherein said fuel-filtering material comprises zinc oxide.

6. The system of claim 1, wherein said fuel-filtering material comprises activated carbon.

7. The system of claim 1, wherein said cartridge further comprises at least one radially routed orifice, with respect to said fUel flow pat, extending from said fuel flow path to an outer surface of said cartridge, wherein said radially routed orifice is disposed in said fuel flow path prior to said fuel-filtering material to provide unfiltered fuel to said outer surface of said cartridge for leak detection if said cartridge is not properly sealed to said fuel container.

8. The system of claim 7, wherein said radially routed orifice releases unfiltered fuel from said cartridge when said cartridge is not properly sealed to said fuel container.

9. The system of claim 1, wherein said fuel flow path fluidly couples said frel container with said fuel cell system.

10. The system of claim 1, wherein said cartridge further comprises a second coupler disposed on said proximal end of said body to fluidly couple said cartridge to said fuel cell system.

11. The system of claim 10, wherein said second coupler comprises external threads.

12. The system of claim 10, wherein said second coupler is configured to fluidly couple said cartridge to a reformer of said fuel cell system so as to produce hydrogen from said fuel.

13. The system of claim 10, wherein said second coupler further comprises at least one O-ring for providing a seal for the coupling between said cartridge and said fbel cell system.

14. The system of claim 10, further comprising a separate inline filter for odorants disposed between said fuel cell system and said fuel-filtering material, wherein said second coupler is coupled with said separate, inline filter for odorants.

15. The system of claim 1, wherein said fuel cell system comprising a fuel cell system coupler having a valve actuator that activates a valve of said fuel container when said fuel container and cartridge are coupled to said fuel cell system through said fuel cell system coupler, wherein said cartridge further comprises an actuator orifice that is configured to receive said valve actuator.

16. The system of claim 15, wherein said actuator orifice further provides a leak detection path for escape of unfiltered fuel when said cartridge is not properly connected to said fuel cell system coupler.

17. The system of claim 1, further comprising a plurality of passages running through said body of said cartridge, said passages containing said fuel-filtering material.

18. The system of claim 17, wherein said plurality of passages are arranged around a central actuator orifice for receiving a valve actuator to actuate a valve of said fuel container.

19. The system of claim 18, further comprising at least one O-ring in said actuator orifice to seal said actuator orifice and prevent fuel leakage through said actuator orifice.

20. The system of claim 1, wherein said odorant comprises sulfur.

21. The system of claim 1, further comprising at least one radially routed orifice, with respect to said fuel flow path, extending from said fuel flow path to, and opening on, an outer surface of said cartridge, wherein said radially routed orifice is disposed in said fuel flow path prior to said fuel-filtering material and on said outer surface between two O-rings disposed on said outer surface.

22. The system of claim 1, wherein said cartridge is integrated with said fuel container into said single unit.

23. The system of claim 1, wherein said cartridge is configured to directly couple with said fuel container.

24. An odorized fuel system comprising an odorant removal cartridge for use with a fuel container, said system comprising:
said fuel container configured to hold a quantity of an odorized fuel; and
said odorant removal cartridge coupled to said fuel container, wherein said cartridge comprises:
a body with a distal and a proximal end;
a fuel flow path that extends through said body from said distal end to said proximal end;
a first coupler disposed on said distal end of said body that fluidly couples said odorant removal cartridge to an outlet on an exterior of said fuel container; and
a fuel-filtering material disposed in said fuel flow path that removes said odorant from fuel in said fuel flow path;
wherein said fuel container and said odorant removal cartridge are simultaneously replaced as a single unit.

25. The system of claim 24, wherein said first coupler comprises internal threads disposed on said distal end of said odorant removal cartridge.

26. The system of claim 24, wherein said fuel-filtering material comprises a porous matrix material.

27. The system of claim 24, wherein said odorant removal cartridge further comprises at least one radially routed orifice, with respect to said fuel flow path, providing an pathway from said fuel flow path to an outer surface of said cartridge, wherein said radially routed orifice is disposed along said fuel flow path prior to said fuel-filtering material so as to release unfiltered fuel to said outer surface of said odorant removal cartridge for leak detection if said cartridge is not properly sealed to said fuel container.

28. The system of claim 24, wherein said tel flow path fluidly couples said fuel container with a fuel cell system through said odorant removal cartridge, wherein said odorant removal cartridge further comprises a second coupler disposed on said proximal end of said body that is fluidly coupled with said fuel cell system.

29. The system of claim 28, wherein said second coupler comprises external threads.

30. The system of claim 28, wherein said second coupler is fluid coupled with a reformer of said fuel cell system.

31. The system of claim 30, wherein said actuator orifice further provides a leak detection path for escape of unfiltered fuel when said cartridge is not properly connected to said frel cell system coupler.

32. The system of claim 24, wherein said odorant removal cartridge further comprises an actuator orifice that receives a valve actuator of a fuel cell system coupler that activates a valve of said fuel container when said fuel container and odorant removal cartridge are coupled to a fuel cell system with said fuel cell system coupler.

33. The system of claim 24, further comprising at least one radially routed orifice, with respect to said fuel flow path, extending from said fuel flow path to, and opening onto, an outer suiface of said cartridge, wherein said radially routed orifice is disposed along said fuel flow path prior to said fuel-filtering material and on said outer surface between two O-rings disposed on said outer surface.

34. The system of claim 24. wherein said odorant removal cartridge is integrated with said fuel container into said single unit.

35. The system of claim 24, wherein said odorant removal cartridge further comprises a second coupler disposed on said proximal end of said body that is fluidly coupled with a separate, in-line filter for odorants.

36. The system of claim 24, wherein said odorant removal cartridge is directly coupled with said fuel container.

* * * * *

UNITED STATES PATENT AND TRADEMARK OFFICE
CERTIFICATE OF CORRECTION

| | | |
|---|---|---|
| PATENT NO. | : 7,419,060 B2 | Page 1 of 1 |
| APPLICATION NO. | : 10/382701 | |
| DATED | : September 2, 2008 | |
| INVENTOR(S) | : Alan R Arthur et al. | |

It is certified that error appears in the above-identified patent and that said Letters Patent is hereby corrected as shown below:

In column 8, line 47, in Claim 1, delete "pat tat" and insert -- path that --, therefor.

In column 8, line 53, in Claim 1, delete "pat tat" and insert -- path that --, therefor.

In column 8, line 60, in Claim 3, delete "af" and insert -- of --, therefor.

In column 9, line 3, in Claim 7, delete "fUel" and insert -- fuel --, therefor.

In column 9, line 3, in Claim 7, delete "pat" and insert -- path --, therefor.

In column 9, line 13, in Claim 9, delete "frel" and insert -- fuel --, therefor.

In column 9, line 25, in Claim 13, delete "fbel" and insert -- fuel --, therefor.

In column 9, line 57, in Claim 21, delete "betwecn" and insert -- between --, therefor.

In column 10, line 29, in Claim 28, delete "tel" and insert -- fuel --, therefor.

In column 10, line 39, in Claim 31, delete "claim 30" and insert -- claim 32 --, therefor.

In column 10, line 41, in Claim 31, delete "frel" and insert -- fuel --, therefor.

In column 10, line 52, in Claim 33, delete "suiface" and insert -- surface --, therefor.

In column 10, line 57, in Claim 34, delete "claim 24." and insert -- claim 24, --, therefor.

Signed and Sealed this

Thirty-first Day of March, 2009

JOHN DOLL
*Acting Director of the United States Patent and Trademark Office*